United States Patent [19]

Jonas et al.

[11] Patent Number: 5,137,885
[45] Date of Patent: Aug. 11, 1992

[54] THIADIAZINONES

[75] Inventors: Rochus Jonas; Ingeborg Lues, both of Darmstadt; Norbert Beier, Reinheim; Michael Klockow, Rossdorf; Klaus-Otto Minck, Ober-Ramstadt, all of Fed. Rep. of Germany

[73] Assignee: Merck Patent Gesellschaft Mit Beschraenkter Haftung, Darmstadt, Fed. Rep. of Germany

[21] Appl. No.: 811,212

[22] Filed: Dec. 20, 1991

[30] Foreign Application Priority Data

Dec. 21, 1990 [DE] Fed. Rep. of Germany ....... 4041074

[51] Int. Cl.$^5$ .................. C07D 285/16; A61K 31/54
[52] U.S. Cl. ...................................... 514/222.5; 544/8
[58] Field of Search ........................... 544/8; 514/222.5

[56] References Cited

U.S. PATENT DOCUMENTS 4,933,336 6/1990 Martin et al. ............................ 544/8

FOREIGN PATENT DOCUMENTS 294647 12/1988 European Pat. Off. ................ 544/8

Primary Examiner—John M. Ford
Attorney, Agent, or Firm—Millen, White & Zelano

[57] ABSTRACT

Thiadiazinones of the formula I

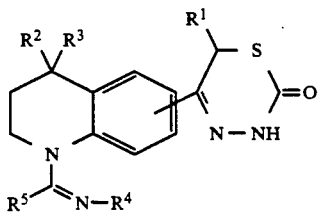

in which $R^1$, $R^2$, $R^3$, $R^4$ and $R^5$ have the meaning given in claim 1, show positively inotropic and vasodilating action and are suitable for combating cardiovascular diseases.

10 Claims, No Drawings

THIADIAZINONES

SUMMARY OF THE INVENTION

The invention relates to novel thiadiazinone derivatives of the formula I

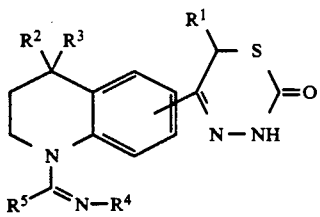

in which
R$^1$, R$^2$ and R$^3$ are each H or A,
R$^4$ is H, A, Ar, Ar-alkyl or cycloalkyl having 3-7 C atoms,
R$^5$ is A, Ar or cycloalkyl having 3-7 atoms,
A is alkyl having 1-8 C atoms,
Ar is an unsubstituted phenyl radical or a phenyl radical mono-, di- or trisubstituted by A, OH, OA, SR$^6$, SOR$^6$, SO$_2$R$^6$, Hal, NH$_2$, NHA, NA$_2$, NO$_2$, O-CH$_2$-O or CO-A,
"-alkyl" is alkylene having 1-5 C atoms,
R$^6$ is A or Ar and
Hal is F, Cl, Br or I
and salts thereof.

Thiadiazinone derivatives, which correspond to the formula I, but in which the nitrogen atom of the quinoline radical is substituted by an H atom or an acyl radical, are disclosed in EP 294,647.

The invention was based on the object of discovering novel compounds with useful properties, in particular those which can be used for the preparation of medicaments.

It has been found that the compounds of the formula I have useful pharmacological properties, coupled with good tolerability. In particular, they exhibit an action on the force of the heart (positively inotropic activity); the substances furthermore have a vasodilating action and therefore promote circulation. The vasodilating action and the cardiac action can be determined, for example, on anaesthetised or conscious dogs, cats, monkeys or mini-pigs, and the positively inotropic action can also be determined on isolated heart preparations (for example atrium, papillary muscle or perfused whole heart) from rats, guinea pigs, cats or dogs, for example in accordance with methods such as are described in Arzneimittelforschung, Volume 31 (I) No. 1a (1981), pages 141 to 170, or by Schliep et al. in 9th International Congress of Pharmacol., London, Abstracts of papers 9P.

Moreover, the compounds are distinguished in that they cause an increase in the Ca sensitivity of the contractile proteins and fewer side effects, such as, for example, arrhythmias, in comparison to other substances having positively inotropic action.

Antithrombotic and platelet aggregation-inhibiting properties and properties which influence the shape of erythrocytes furthermore are possessed by these compounds. The influencing of platelet function in the sense of inhibition of aggregation can be demonstrated on rats ex vivo in the test in accordance with the method of Born (Nature 194, 927-929, 1962). The antithrombotic action manifests itself in the increase in bleeding time in accordance with the method of Stella (Thrombos. Res. 7, 709-716, 1975), in the reduction in the thrombus weight on thrombosing of the jugular vein in rats induced by low temperatures in accordance with the method of Meng (Ther. Ber. 47, 69-79, 1975) and in the increase of the laser pulse required for complete thrombosing in the mesenteric venules of rats in accordance with a modification of the method of Kovacs (Microvasc. Res. 6, 194-201, 1973).

The favorable action on erythrocyte deformability can be detected in a nucleopore filter by the method of Schmid-Schönbein (Pflüger's Archiv 338, 93-114, 1973). Favorable effects on the fibrinolysis/euglobulinolysis time can also be determined in accordance with the method of v. Kaulla (Progr. Chem. Fibrinol., Thrombol. 1, 131-149, 1975; ed J. F. Davidson, Raven Press, N.Y.).

The compounds can therefore be used as medicaments compounds in human and veterinary medicine. They can furthermore be used as intermediate products for the preparation of further medically active compounds.

The invention accordingly relates to the compounds of the formula I, the acid addition salts thereof and a process for their preparation, characterized in that a compound of the formula II

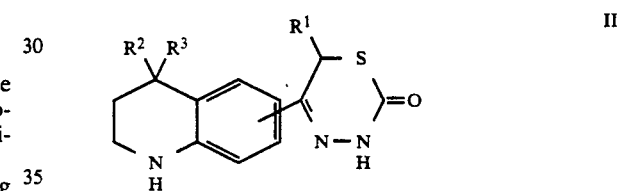

in which R$^1$, R$^2$ and R$^3$ have the meanings indicated, is reacted with an imide chloride of the formula III

R$^5$—CCl=NR$^4$  III in which R$^4$ and R$^5$ have the meanings indicated, or in that a ketone of the formula IV

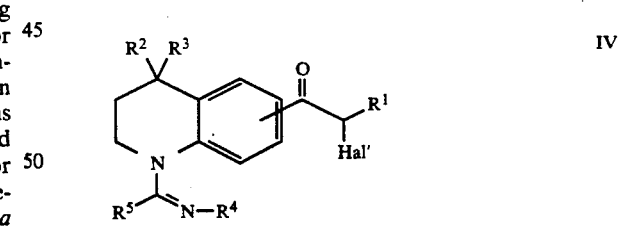

in which
R$^1$, R$^2$, R$^3$, R$^4$ and R$^5$ have the meanings indicated
and Hal'
is Cl, Br or I,
is reacted with a compound of the formula V

H$_2$N—NH—CS—OR  V in which R is alkyl having 1-5 C atoms or an equivalent of a metal or ammonium cation,
or in that, for the preparation of a compound of the formula I in which R$^4$ is H, a corresponding compound which, however, carries an amino protective group instead of R$^4$ is treated with a hydrolysing or hydrogenolysing agent, or in that, for the preparation of a compound of the formula I in which R⁴ is H, a halomagnesium compound of the formula VI

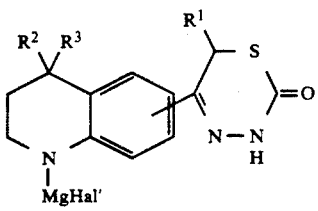

in which R¹, R², R³ and Hal' have the meanings indicated, is reacted with a nitrile of the formula VII

R⁵—CN  VII in which
R⁵ has the meaning indicated,
and the product obtained is then hydrolysed,
and in that, if desired, in a thiadiazinone derivative of the formula I one or both radical(s) R⁴ and/or R⁵ is/are converted into (an)other radical(s) R⁴ and/or R⁵ and/or a base of the formula I obtained is converted by treatment with an acid into one of its acid addition salts.

Above and below, R¹ to R⁶, A, Ar, "-alkyl", Hal, Hal' and R have the meanings indicated in the formulae I, IV and V, if not expressly stated otherwise.

In the formulae, A is an alkyl radical having 1-8 C atoms, which are preferably unbranched and preferably have 1, 2, 3, 4 or 5 C atoms, preferably methyl, in addition preferably ethyl or propyl, and furthermore preferably isopropyl, butyl, isobutyl, sec-butyl, tertbutyl, n-pentyl or isopentyl, as well as branched or unbranched hexyl, heptyl and octyl.

The radical Ar can be unsubstituted phenyl, but is preferably monosubstituted, particularly preferably disubstituted phenyl, where the substituents can be identical or different and are preferably in the paraposition or in the para- and meta-position respectively. Particularly preferred substituents are methoxy and fluorine, but also hydroxyl, chlorine and ethoxy.

In particular, Ar is preferably p-fluorophenyl or 3,4-dimethoxyphenyl.

The group "-alkyl" is a straight-chain or branched alkylene group, preferably —CH₂— or —CH₂—CH₂—.

Cycloalkyl can contain 3-7 C atoms, but preferably has 5 or 6 C atoms and is preferably cyclopentyl or cyclohexyl.

The dihydrothiadiazinone ring is preferably in the 6-position, furthermore preferably in the 7-position of the tetrahydroquinoline system; but it can also be in the 5- or 8-position.

The radicals R¹, R² and R³ are preferably each H or methyl.

The radical R⁴ is preferably H or ethyl, furthermore preferably cyclopentyl, methyl, propyl, isopropyl, butyl or isopentyl.

The radical R⁵ is preferably phenyl, particularly preferably substituted phenyl, preferably p-fluorophenyl or 3,4-dimethoxyphenyl.

The invention particularly relates to those compounds of the formula I in which at least one of the radicals mentioned has one of the abovementioned preferred meanings.

Some preferred groups of compounds can be expressed by the following part-formulae Ia to If, which correspond to the formula I and in which the radicals which are not described in more detail have the meaning given in the formula I, but in which in Ia, the dihydrothiadiazinone ring is in the 6-position,
R¹, R² and R³ are each H or methyl,
R⁴ is alkyl having 1-5 C atoms and
R⁵ is mono- or disubstituted phenyl;

in Ib, the dihydrothiadiazinone ring is in the 6-position,
R¹, R² and R³ are each H or methyl,
R⁴ is cycloalkyl and
R⁵ is mono- or disubstituted phenyl;

in Ic, the dihydrothiadiazinone ring is in the 6-position,
R¹, R² and R³ are each H or methyl,
R⁴ is H and
R⁵ is mono- or disubstituted phenyl;

in Id, the dihydrothiadiazinone ring is in the 6-position,
R¹, R² and R³ are each H or methyl,
R⁴ is alkyl having 1-5 C atoms and
R⁵ is p-fluorophenyl, 3-chloro-4-methoxyphenyl or 3,4-dimethoxyphenyl;

in Ie, the dihydrothiadiazinone ring is in the 6-position,
R¹, R² and R³ are each H or methyl,
R⁴ is cycloalkyl and
R⁵ is p-fluorophenyl, 3-chloro-4-methoxyphenyl or 3,4-dimethoxyphenyl;

in If, the dihydrothiadiazinone ring is in the 6-position,
R¹, R² and R³ are each H or methyl,
R⁴ is H and
R⁵ is p-fluorophenyl, 3-chloro-4-methoxyphenyl or 3,4-dimethoxyphenyl.

The compounds of the formula I are moreover prepared by methods which are known per se, such as are described in the literature (for example in the standard works, such as Houben-Weyl, Methoden der Organischen Chemie (Methods of Organic Chemistry), Georg-ThiemeVerlag, Stuttgart), and in particular under reaction conditions which are known and suitable for the reactions mentioned. In selecting these conditions it is possible to make use of variants which are known per se and are not mentioned in more detail here.

If desired, the starting substances for the claimed process can also be formed in situ such that they are not isolated from the reaction mixture but are immediately reacted further to give the compounds of the formula I.

The starting substances of the formulae II and III are known in some cases. Where they are not known, they can be prepared by methods which are known per se. The preparation of the compounds of the formula II is known from EP 294,647.

Specifically, the reaction of the compounds of the formula II with the compounds of the formula III is carried out in the presence or absence of an inert solvent at temperatures between about −20° and about +150°, preferably between 20° and 100°. Examples of suitable solvents are hydrocarbons, such as benzene, toluene, xylenes or mesitylene; halogenated hydrocarbons, such as dichloromethane, trichloroethylene or chlorobenzene; alcohols, such as methanol, ethanol or isopropanol; glycols and glycol ethers, such as ethylene glycol, diethylene glycol and 2-methoxyethanol; nitriles, such as acetonitrile; ethers, such as tetrahydrofuran or dioxane; amides, such as dimethylformamide (DMF); and sulfoxides, such as dimethyl sulfoxide. Mixtures of these solvents are also suitable.

In the compounds of the formula IV, Hal' is preferably Cl or Br.

In the compounds of the formula V, R is preferably methyl or ethyl, but also Na, K or $NH_4$.

If desired, the starting substances can also be formed in situ such that they are not isolated from the reaction mixture, but are immediately reacted further to give the compounds of the formula I. On the other hand, it is possible to carry out the reaction stepwise, it being possible to isolate further intermediate products.

The starting substances of the formulae IV and V are known in some cases. Where they are not known, they can be prepared by methods which are known per se. The ketones of the formula IV are accessible, for example, by Friedel-Crafts synthesis from corresponding tetrahydroquinoline derivatives using compounds of the formula Hal'—CO—$CHR^2$—Hal'.

Specifically, the reaction of the ketones of the formula IV with the compounds of the formula V is carried out under conditions which have been previously indicated for the reaction between compounds of the formulae II and III.

A compound of the formula I can also be obtained by treating a compound which otherwise corresponds to the formula I, but carries an "amino protective group" instead of $R^4$, with a reagent which reductively removes this "protective group".

"Protective groups" used are preferably $CO_2$—$CH_2C_6H_5$, particularly preferably OH, which can preferably be removed by transition metal carbonyls, particularly preferably by iron pentacarbonyl, but also by $Fe_2(CO)_9$ at temperatures between about $-20°$ and about $+150°$, preferably between 20° and 100°, in the presence or absence of an inert solvent.

Suitable solvents are, for example, those indicated above for the reaction of II with III.

Compounds of the formula I can also be obtained by reacting a halomagneisum compound of the formula VI with a nitrile of the formula VII and then hydrolysing the product obtained.

Compounds of the formulae VI and VII are known per se or can be prepared by methods which are known per se.

These reactions are preferably carried out under conditions which are known for Grignard reactions or other organometallic reactions, advantageously in the presence or absence of an inert solvent at temperatures between about $-20°$ and about $+150°$, preferably between 0° and 150°. Suitable solvents are those indicated above, as long as they cannot react with the compounds of the formula VI themselves.

It is also possible to convert one or both radical(s) $R^4$ and/or $R^5$ into (an)other radical(s) $R^4$ and/or $R^5$. Using reactions known per se, for example, an $NO_2$ group can be reduced to an $NH_2$ group, an $NH_2$ or NHA group can be alkylated, an OH group can be etherified or else an aryl ether can be cleaved. Moreover, substituents of these radicals $R^4$ and/or $R^5$, such as, for example, S-$R^6$ or SO-$R^6$ groups can be oxidised if the reactions take place selectively at the radicals $R^4$ and/or $R^5$.

A base of the formula I can be converted with an acid into the associated acid addition salt. Possible acids for this reaction are, in particular, those which give physiologically acceptable salts. It is thus possible to use inorganic acids, for example sulfuric acid, nitric acid, hydrogen halide acids, such as hydrochloric acid or hydrobromic acid, phosphoric acids, such as orthophosphoric acid, or sulfamic acid, and furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and -disulfonic acids and laurylsulfuric acid. Salts with physiologically unacceptable acids, for example picrates, can be used to purify the compounds of the formula I.

Compounds of the formula I can contain one or more centres of asymmetry. In this case, they are usually present in racemic form. Racemates obtained can be resolved mechanically or chemically into their optical antipodes by methods which are known per se. Preferably, diastereomers are formed from the racemic mixture by reaction with an optically active resolving agent. Suitable resolving agents for basic compounds of the formula I are, for example, optically active acids, such as the D- and L-forms of tartaric acid, diacetyltartaric acid, dibenzoyltartaric acid, mandelic acid, malic acid and lactic acid, or the various optically active camphorsulfonic acids, such as $\beta$-camphorsulfonic acid or else optically active camphanic acid or other optically active terpenoic acids.

It is of course also possible to obtain optically active compounds of the formula I by the methods described above by using starting substances which are already optically active.

Moreover, the compounds of the formula I, in analogy to the E-Z isomerism in C=C double bonds, show a comparable stereoisomerism to the non-cyclic C=N double bond. The compounds can thus be present as mixtures of the possible stereoisomers or as pure E- or Z-isomers.

The invention furthermore relates to the use of the compounds of the formula I and their physiologically acceptable salts for the preparation of pharmaceutical formulations, in particular by a non-chemical route. They can here be brought into a suitable dosage form together with at least one solid, liquid and/or semi-liquid excipient or auxiliary and, if appropriate, in combination with one or more further active compounds.

The invention furthermore relates to agents, in particular pharmaceutical formulations, containing at least one compound of the formula I and/or one of its physiologically acceptable salts.

These formulations can be used as medicaments in human or veterinary medicine. Possible excipients are organic or inorganic substances which are suitable for enteral (for example oral), parenteral or topical administration and do not react with the novel compounds, for example water, vegetable oils, benzyl alcohols, polyethylene glycols, glycerol triacetate, gelatine, carbohydrates, such as lactose or starch, magnesium stearate, talc or petroleum jelly. Tablets, coated tablets, capsules, syrups, elixirs or drops are used, in particular, for oral administration, suppositories are used for rectal administration, solutions, preferably oily or aqueous solutions, and furthermore suspensions, emulsions or implants are used for parenteral administration, and ointments, creams or powders are used for topical application. The novel compounds can also be lyophilised and the lyophilisates obtained can be used, for example, for the production of injection preparations. The formulations mentioned can be sterilised and/or contain auxiliaries, such as lubricants, preservatives, stabilisers and/or wetting agents, emulsifiers, salts for influencing the osmotic pressure, buffer substances, colouring substances, flavouring substances and/or aroma substances. If desired, they can also contain one or more further active compounds, for example one or more vitamins.

The compounds of the formula I can be used in combating diseases, in particular cardiac insufficiency and hypertension, and in the therapeutic treatment of the human or animal body.

The substances according to the invention are thereby as a rule administered in analogy to known positively inotropically active substances, such as amrinone, preferably in dosages of between about 1 and 100 mg, in particular between 2 and 20 mg per dosage unit. The daily dosage is preferably between about 0.02 and 2 mg/kg of body weight. However, the specific dose for each particular patient depends on the most diverse factors, for example on the activity of the specific compound used, on the age, body weight, general state of health, sex, on the diet, on the administration time and route and on the rate of excretion, medicament combination and severity of the particular disease to which the therapy applies. Oral administration is preferred. In contrast to the digitalis glycosides used to date for the therapy of cardiac insufficiency, the compounds of the formula I are distinguished by an improved therapeutic range and peripheral relief.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees celsius; and, unless otherwise indicated, all parts and percentages are by weight.

The entire disclosure of all applications, patents and publications, cited above and below, and of corresponding German Application P 40 41 074.9, filed Dec. 21, 1990, are hereby incorporated by reference.

In the following examples, "customary working up" means:

Water or dilute sodium hydroxide solution is added if necessary, the mixture is extracted with an organic solvent, such as ethyl acetate, chloroform or dichloromethane, the phases are separated, the organic phase is dried over sodium sulfate, filtered and evaporated, and the residue is purified by chromatography and/or crystallisation.

The solidification points given refer to the free bases and/or the hydrochlorides on which they are based.

EXAMPLE 1

A solution of 2.6 g of 5-(1,2,3,4-tetrahydroquinolin-6-yl)-6-methyl-3,6-dihydro-2H-1,3,4-thiadiazin-2-one ("A") in 40 ml of dichloromethane, to which 1 ml of pyridine is added, is treated with 2.1 g of N-ethyl-3,4-dimethoxybenzoic acid imide chloride, dissolved in 20 ml of dichloromethane, in the cold and stirred for 1 hour. After removal of the solvent, customary working gives 5-[1-(N-ethyl-3,4-dimethoxybenzimidoyl)-1,2,3,4-tetrahydroquinolin-6-yl]-6-methyl-3,6-dihydro-2H-1,3,4-thiadiazin-2-one, m.p. 208°. Hydrochloride, m.p. 247°.

The following are obtained analogously:
from "A" and N-isopropyl-3,4-dimethoxybenzoic acid imide chloride
5-[1-(N-isopropyl-3,4-dimethoxybenzimidoyl)-1,2,3,4-tetrahydroquinolin-6-yl]-6-methyl-3,6-dihydro-2H-1,3,4-thiadiazin-2-one, m.p. 250°; from "A" and N-cyclopentyl-3,4-dimethoxybenzoic acid imide chloride
5-[1-(N-cyclopentyl-3,4-dimethoxybenzimidoyl)-1,2,3,4-tetrahydroquinolin-6-yl]-6-3,6-dihydro-2H-1,3,4-thiadiazin-2-one, m.p. 258°; from "A" and N-(2-methylbutyl)-3,4-dimethoxybenzoic acid imide chloride
5-[1-(N-(2-methylbutyl)-3,4-dimethoxybenzimdoyl)-1,2,3,4-tetrahydroquinolin-6-yl]-6-methyl-3,6-dihydro-2H-1,3,4-thiadiazin-2-one, m.p. 253°;
from "A" and N-cyclopropyl-3,4-dimethoxybenzoic acid imide chloride
5-[1-(N-cyclopropyl-3,4-dimethoxybenzimidoyl)-1,2,3,4-tetrahydroquinolin-6-yl]-6-methyl-3,6-dihydro-2H-1,3,4-thiadiazin-2-one, m.p. 218°; hydrochloride, m.p. 242°; from "A" and N-methyl-3-chloro-4-methoxybenzoic acid imide chloride
5-[1-(N-methyl-3-chloro-4-methoxybenzimidoyl)-1,2,3,4-tetrahydroquinolin-6-yl]-6-methyl-3,6-dihydro-2H-1,3,4-thiadiazin-2-one, m.p. 229°; hydrochloride, m.p. 252°; from "A" and N-isopropyl-3-chloro-4-methoxybenzoic acid imide chloride
5-[1-(N-isopropyl-3-chloro-4-methoxybenzimidoyl)-1,2,3,4-tetrahydroquinolin-6-yl]-6-methyl-3,6-dihydro-2H-1,3,4-thiadiazin-2-one, m.p. 240°; from "A" and N-phenyl-3,4-dimethoxybenzoic acid imide chloride
5-[1-(N-phenyl-3,4-dimethoxybenzimidoyl)-1,2,3,4-tetrahydroquinolin-6-yl]-6-methyl-3,6-dihydro-2H-1,3,4-thiadiazin-2-one;
from "A" and N-phenyl-3-chloro-4-methoxybenzoic acid imide chloride
5-[1-(N-phenyl-3-chloro-4-methoxybenzimidoyl)-1,2,3,4-tetrahydroquinolin-6-yl]-6-methyl-3,6-dihydro-2H-1,3,4-thiadiazin-2-one;
from "A" and N-ethyl-p-fluorobenzoic acid imide chloride
5-[1-(N-ethyl-p-fluorobenzimidoyl)-1,2,3,4-tetrahydroquinolin-6-yl]-6-methyl-3,6-dihydro-2H-1,3,4-thiadiazin-2-one, m.p. 264°;
from "A" and N-butyl-3,4-dimethoxybenzoic acid imide chloride
5-[1-(N-butyl-3,4-dimethoxybenzimidoyl)-1,2,3,4-tetrahydroquinolin-6-yl]-6-methyl-3,6-dihydro-2H-1,3,4-thiadiazin-2-one.

EXAMPLE 2

5-[1-(N-butyl-3,4-dimethoxybenzimidoyl)-4,4-dimethyl-1,2,3,4-tetrahydroquinolin-6-yl]-6-methyl-3,6-dihydro-2H-1,3,4-thiadiazin-2-one, m.p. 253°, is obtained from 5-(4,4-dimethyl-1,2,3,4-tetrahydroquinolin-6-yl)-6-methyl-3,6-dihydro-2H-1,3,4-thiadiazin-2-one ("B") and N-butyl-3,4-dimethoxybenzoic acid imide chloride analogously to Example 1.

The following are obtained analogously: from "B" and N-cyclohexyl-3,4-dimethoxybenzoic acid imide chloride 5-[1-(N-cyclohexyl-3,4-dimethoxybenzimidoyl)-4,4-dimethyl-1,2,3,4-tetrahydroquinolin-6-yl]-6-methyl-3,6-dihydro-2H-1,3,4-thiadiazin-2-one;

from "B" and N-cyclopropyl-3,4-dimethoxybenzoic acid imide chloride
5-[1-(N-cyclopropyl-3,4-dimethoxybenzimidoyl)-4,4-dimethyl-1,2,3,4-tetrahydroquinolin-6-yl]-6-methyl-3,6-dihydro-2H-1,3,4-thiadiazin-2-one;

from "B" and N-cyclopentyl-3,4-dimethoxybenzoic acid imide chloride
5-[1-(N-cyclopentyl-3,4-dimethoxybenzimidoyl)-4,4-dimethyl-1,2,3,4-tetrahydroquinolin-6-yl]-6-methyl-3,6-dihydro-2H-1,3,4-thiadiazin-2-one;

from "B" and N-ethyl-3,4-dimethoxybenzoic acid imide chloride
5-[1-(N-ethyl-3,4-dimethoxybenzimidoyl)-4,4-dimethyl-1,2,3,4-tetrahydroquinolin-6-yl]-6-methyl-3,6-dihydro-2H-1,3,4-thiadiazin-2-one;

from "B" and N-ethyl-p-fluorobenzoic acid imide chloride 5-[1-(N-ethyl-p-fluorobenzimidoyl)-4,4-dimethyl-1,2,3,4-tetrahydroquinolin-6-yl]-6-methyl-3,6-dihydro-2H-1,3,4-thiadiazin-2-one;

from "B" and N-isopropyl-p-fluorobenzoic acid imide chloride
5-[1-(N-isopropyl-p-fluorobenzimidoyl)-4,4-dimethyl-1,2,3,4-tetrahydroquinolin-6-yl]-6-methyl-3,6-dihydro-2H-1,3,4-thiadiazin-2-one;

from "B" and N-methyl-3-chloro-4-methoxybenzoic acid imide chloride
5-[1-(N-methyl-3-chloro-4-methoxybenzimidoyl)-4,4-dimethyl-1,2,3,4-tetrahydroquinolin-6-yl]-6-methyl-3,6-dihydro-2H-1,3,4-thiadiazin-2-one;

from "B" and N-isopropyl-3-chloro-4-methoxybenzoic acid imide chloride
5-[1-(N-isopropyl-3-chloro-4-methoxybenzimidoyl)-4,4-dimethyl-1,2,3,4-tetrahydroquinolin-6-yl]-6-methyl-3,6-dihydro-2H-1,3,4-thiadiazin-2-one.

EXAMPLE 3

1 equivalent of iron pentacarbonyl is added dropwise to a solution of 2.9 g of 5-[1-(N-hydroxy-3,4-dimethoxybenzimidoyl)-1,2,3,4-tetrahydroquinolin-6-yl]-6-methyl-3,6-dihydro-2H-1,3,4-thiadizain-2-one (obtainable from N-hydroxy-3,4-dimethoxybenzoic acid imide chloride) and 5-(1,2,3,4-tetrahydroquinolin-6-yl)-6-methyl-3,6-dihydro-2H-1,3,4-thiadiazin-2-one) in 30 ml of tetrahydrofuran. The reaction mixture is boiled for 2 hours and worked up in the customary manner. 5-[1-(3,4-Dimethoxybenzimidoyl)-1,2,3,4-tetrahydroquinolin-6-yl)]-6-methyl-3,6-dihydro-2H-1,3,4-thiadiazin-2-one, m.p. 228°, is obtained.

The following are obtained analogously by boiling with iron pentacarbonyl:

from 5-[1-(N-hydroxy-p-fluorobenzimidoyl)-1,2,3,4-tetrahydroquinolin-6-yl]-6-methyl-3,6-dihydro-2H-1,3,4-thiadiazin-2-one 5-[1-(p-fluorobenzimidoyl)-1,2,3,4-tetrahydroquinolin-6-yl]-6-methyl-3,6-dihydro-2H-1,3,4-thiadiazin-2-one, m.p. 267°;

from 5-[1-(N-hydroxy-3,4-dimethoxybenzimidoyl)-4,4-dimethyl-1,2,3,4-tetrahydroquinolin-6-yl]-6-methyl-3,6-dihydro-2H-1,3,4-thiadiazin-2-one 5-[1-(3,4-dimethoxybenzimidoyl)-4,4-dimethyl-1,2,3,4-tetrahydroquinolin-6-yl]-6-methyl-3,6-dihydro-2H-1,3,4-thiadiazin-2-one;

from 5-[1-(N-hydroxy-p-fluorobenzimidoyl)-4,4-dimethyl-1,2,3,4-tetrahydroquinolin-6-yl]-6-methyl-3,6-dihydro-2H-1,3,4-thiadiazin-2-one 5-[1-(p-fluorobenzimidoyl)-4,4-dimethyl-1,2,3,4-tetrahydroquinolin-6-yl]-6-methyl-3,6-dihydro-2H-1,3,4-thiadiazin-2-one;

from 5-[1-(N-hydroxy-3-chloro-4-methoxybenzimidoyl)-1,2,3,4-tetrahydroquinolin-6-yl]-6-methyl-3,6-dihydro-2H-1,3,4-thiadiazin-2-one 5-[1-(3-chloro-4-methoxybenzimidoyl)-1,2,3,4-tetrahydroquinolin-6-yl]-6-methyl-3,6-dihydro-2H-1,3,4-thiadiazin-2-one;

from 5-[1-(N-hydroxy-p-fluorobenzimidoyl)-1,2,3,4-tetrahydroquinolin-6-yl]-6-ethyl-3,6-dihydro-2H-1,3,4-thiadiazin-2-one 5-[1-(p-fluorobenzimidoyl)-1,2,3,4-tetrahydroquinolin-6-yl]-6-ethyl-3,6-dihydro-2H-1,3,4-thiadiazin-2-one;

from 5-[1-(N-hydroxy-3-chloro-4-methoxybenzimidoyl)-4,4-dimethyl-1,2,3,4-tetrahydroquinolin-6-yl]-6-ethyl-3,6-dihydro-2H-1,3,4-thiadiazin-2-one 5-[1-(3-chloro-4-methoxybenzimidoyl)-4,4-dimethyl-1,2,3,4-tetrahydroquinolin-6-yl]-6-ethyl-3,6-dihydro-2H-1,3,4-thiadiazin-2-one;

from 5-[1-(N-hydroxy-p-fluorobenzimidoyl)-4,4-dimethyl-1,2,3,4-tetrahydroquinolin-6-yl]-6-isopropyl-3,6-dihydro-2H-1,3,4-thiadiazin-2-one 5-[1-(p-fluorobenzimidoyl)-4,4-dimethyl-1,2,3,4-tetrahydroquinolin-6-yl]-6-isopropyl-3,6-dihydro-2H-1,3,4-thiadiazin-2-one;

from 5-[1-(N-hydroxy-benzimidoyl)-1,2,3,4-tetrahydroquinolin-6-yl]-6-methyl-3,6-dihydro-2H-1,3,4-thiadiazin-2-one 5-[1-benzimidoyl-1,2,3,4-tetrahydroquinolin-6-yl]-6-methyl-3,6-dihydro-2H-1,3,4-thiadiazin-2-one;

from 5-[1-(N-hydroxy-3,4-dimethoxybenzimidoyl)-4,4-dimethyl-1,2,3,4-tetrahydroquinolin-6-yl]-6-ethyl-3,6-dihydro-2H-1,3,4-thiadiazin-2-one 5-[1-(3,4-dimethoxybenzimidoyl)-4,4-dimethyl-1,2,3,4-tetrahydroquinolin-6-yl]-6-ethyl-3,6-dihydro-2H-1,3,4-thiadiazin-2-one;

from 5-[1-(N-hydroxy-p-fluorobenzimidoyl)-1,2,3,4-tetrahydroquinolin-6-yl]-6-ethyl-3,6-dihydro-2H-1,3,4-thiadiazin-2-one 5-[1-(p-fluorobenzimidoyl)-1,2,3,4-tetrahydroquinolin-6-yl]-6-ethyl-3,6-dihydro-2H-1,3,4-thiadiazin-2-one.

EXAMPLE 4

A solution of 3.1 g of 6-(6-methyl-2-oxo-3,6-dihydro-2H-1,3,4-thiadiazin-5-yl)-1,2,3,4-tetrahydroquinoline-1-magnesium bromide ("C") in 30 ml of tetrahydrofuran is treated dropwise with 1 equivalent of p-fluorobenzonitrile and boiled for 1 hour. Customary working up gives 5-[1-(p-fluorobenzimidoyl)-1,2,3,4-tetrahydroquinolin-6-yl]-6-methyl-3,6-dihydro-2H-1,3,4-thiadiazin-2-one.

The following are obtained analogously from "C"
with benzonitrile 5-(1-benzimidoyl-1,2,3,4-tetrahydroquinolin-6-yl)-6-methyl-3,6-dihydro-2H-1,3,4-thiadiazin-2-one;

with p-chlorobenzonitrile 5-[1-(p-chlorobenzimidoyl)-1,2,3,4-tetrahydroquinolin-6-yl]-6-methyl-3,6-dihydro-2H-1,3,4-thiadiazin-2-one.

EXAMPLE 5

A solution of 2.5 g of 1-(N-isopropyl-p-fluorobenzimidoyl)-6-(2-chloropropionyl)-1,2,3,4-tetrahydroquinoline in 40 ml of acetonitrile is treated with 1 equivalent of O-ethyl hydrazinethioformate and boiled for 2 hours.

Customary working up gives 5-[1-(N-isopropyl-p-fluorobenzimidoyl)-1,2,3,4-tetrahydroquinolin-6-yl]-6-methyl-3,6-dihydro-2H-1,3,4-thiadiazin-2-one.

EXAMPLE 6

5-[1-(N-Butyl-3,4-dimethoxybenzimidoyl)-4,4-dimethyl-1,2,3,4-tetrahydroquinolin-6-yl]-6-ethyl-3,6-dihydro-2H-1,3,4-thiadiazin-2-one is obtained from 5-(4,4-dimethyl-1,2,3,4-tetrahydroquinolin-6-yl)-6-ethyl-3,6-dihydro-2H-1,3,4-thiadiazin-2-one ("D") and N-butyl-3,4-dimethoxybenzoic acid imide chloride after customary working up analogously to Example 1.

The following are obtained analogously:

from "D" and N-cyclohexyl-3,4-dimethoxybenzoic acid imide chloride
5-[1-(N-cyclohexyl-3,4-dimethoxybenzimidoy)-4,4-dimethyl-1,2,3,4-tetrahydroquinolin-6-yl]-6-ethyl-3,6-dihydro-2H-1,3,4-thiadiazin-2-one;

from "D" and N-cyclopropyl-3,4-dimethoxybenzoic acid imide chloride
5-[1-(N-cyclopropyl-3,4-dimethoxybenzimidoyl)-4,4-dimethyl-1,2,3,4-tetrahydroquinolin-6-yl]-6-ethyl-3,6-dihydro-2H-1,3,4-thiadiazin-2-one;

from "D" and N-cyclopentyl-3,4-dimethoxybenzoic acid imide chloride
5-[1-(N-cyclopentyl-3,4-dimethoxybenzimidoyl)-4,4-dimethyl-1,2,3,4-tetrahydroquinolin-6-yl]-6-ethyl-3,6-dihydro-2H-1,3,4-thiadiazin-2-one;

from "D" and N-ethyl-3,4-dimethoxybenzoic acid imide chloride
5-[1-(N-ethyl-3,4-dimethoxybenzimidoyl)-4,4-dimethyl-1,2,3,4-tetrahydroquinolin-6-yl]-6-ethyl-3,6-dihydro-2H-1,3,4-thiadiazin-2-one;

from "D" and N-ethyl-p-fluorobenzoic acid imide chloride
5-[1-(N-ethyl-p-fluorobenzimidoyl)-4,4-dimethyl-1,2,3,4-tetrahydroquinolin-6-yl]-6-ethyl-3,6-dihydro-2H-1,3,4-thiadiazin-2-one;

from "D" and N-isopropyl-p-fluorobenzoic acid imide chloride
5-[1-(N-isopropyl-p-fluorobenzimidoyl)-4,4-dimethyl-1,2,3,4-tetrahydroquinolin-6-yl]-6-ethyl-3,6-dihydro-2H-1,3,4-thiadiazin-2-one;

from "D" and N-methyl-3-chloro-4-methoxybenzoic acid imide chloride
5-[1-(N-methyl-3-chloro-4-methoxybenzimidoyl)-4,4-dimethyl-1,2,3,4-tetrahydroquinolin-6-yl]-6-ethyl-3,6-dihydro-2H-1,3,4-thiadiazin-2-one;

from "D" and N-isopropyl-3-chloro-4-methoxybenzoic acid imide chloride
5-[1-(N-isopropyl-3-chloro-4-methoxybenzimidoyl)-4,4-dimethyl-1,2,3,4-tetrahydroquinolin-6-yl]-6-ethyl-3,6-dihydro-2H-1,3,4-thiadiazin-2-one.

EXAMPLE 7

5-[1-(N-butyl-3,4-dimethoxybenzimidoyl)-4,4-dimethyl-1,2,3,4-tetrahydroquinolin-6-yl]-6-ethyl-3,6-dihydro-2H-1,3,4-thiadiazin-2-one is obtained from 5-(1,2,3,4-tetrahydroquinolin-6-yl)-6-ethyl-3,6-dihydro-2H-1,3,4-thiadiazin-2-one ("E") and N-butyl-3,4-dimethoxybenzoic acid imide chloride, after customary working up analogously to Example 1.

The following are obtained analogously:

from "E" and N-cyclohexyl-3,4-dimethoxybenzoic acid imide chloride
5-[1-(N-cyclohexyl-3,4-dimethoxybenzimidoyl)-1,2,3,4-tetrahydroquinolin-6-yl]-6-ethyl-3,6-dihydro-2H-1,3,4-thiadiazin-2-one;

from "E" and N-cyclopropyl-3,4-dimethoxybenzoic acid imide chloride
5-[1-(N-cyclopropyl-3,4-dimethoxybenzimidoyl)-1,2,3,4-tetrahydroquinolin-6-yl]-6-ethyl-3,6-dihydro-2H-1,3,4-thiadiazin-2-one;

from "E" and N-phenyl-3,4-dimethoxybenzoic acid imide chloride
5-[1-(N-phenyl-3,4-dimethoxybenzimidoyl)-1,2,3,4-tetrahydroquinolin-6-yl]-6-ethyl-3,6-dihydro-2H-1,3,4-thiadiazin-2-one;

from "E" and N-cyclopentyl-3,4-dimethoxybenzoic acid imide chloride
5-[1-(N-cyclopentyl-3,4-dimethoxybenzimidoyl)-1,2,3,4-tetrahydroquinolin-6-yl]-6-ethyl-3,6-dihydro-2H-1,3,4-thiadiazin-2-one;

from "E" and N-ethyl-3,4-dimethoxybenzoic acid imide chloride
5-[1-(N-ethyl-3,4-dimethoxybenzimidoyl)-1,2,3,4-tetrahydroquinolin-6-yl]-6-ethyl-3,6-dihydro-2H-1,3,4-thiadiazin-2-one, m.p. 171°;

from "E" and N-ethyl-p-fluorobenzoic acid imide chloride 5-[1-(N-ethyl-p-fluorobenzimidoyl)-1,2,3,4-tetrahydroquinolin-6-yl]-6-ethyl-3,6-dihydro-2H-1,3,4-thiadiazin-2-one;

from "E" and N-isopropyl-p-fluorobenzoic acid imide chloride
5-[1-(N-isopropyl-p-fluorobenzimidoyl)-1,2,3,4-tetrahydroquinolin-6-yl]-6-ethyl-3,6-dihydro-2H-1,3,4-thiadiazin-2-one;

from "E" and N-methyl-3-chloro-4-methoxybenzoic acid imide chloride
5-[1-(N-methyl-3-chloro-4-methoxybenzimidoyl)-1,2,3,4-tetrahydroquinolin-6-yl]-6-ethyl-3,6-dihydro-2H-1,3,4-thiadiazin-2-one;

from "E" and N-isopropyl-3-chloro-4-methoxybenzoic acid imide chloride
5-[1-(N-isopropyl-3-chloro-4-methoxybenzimidoyl)-1,2,3,4-tetrahydroquinolin-6-yl]-6-ethyl-3,6-dihydro-2H-1,3,4-thiadiazin-2-one.

EXAMPLE 8

A solution of 7.2 g of 5-[1-(N-ethyl-3,4-dimethoxybenzimidoyl)-1,2,3,4-tetrahydroquinolin-6-yl]-6-methyl-3,6-dihydro-2H-1,3,4-thiadiazin-2-one ("F") in 140 ml of tetrahydrofuran is treated with a corresponding amount of S-(+)-camphor-10-sulfonic acid, such that the corresponding diastereomers are obtained in crystalline form. The resolution of the racemate and the isolation of the pure enantiomers is carried out by the customary procedure which is known per se.

Both optical antipodes are obtained:
(+)−"F" m.p. 173°, hydrochloride m.p. 252°;
$[\alpha]_D^{20} = +439.3°$;
(−)−"F" m.p. 173°; hydrochloride m.p. 252°,
$[\alpha]_D^{20} = -433.9°$; (in both cases: c=1 in methanol).

EXAMPLE 9

5-[1-(N-Butyl-3,4-dimethoxybenzimidoyl)-1,2,3,4-tetrahydroquinolin-6-yl]-3,6-dihydro-2H-1,3,4-thiadiazin-2-one is obtained from 5-(1,2,3,4-tetrahydroquinolin-6-yl)-3,6-dihydro-2H-1,3,4-thiadiazin-2-one ("G") and N-butyl-3,4-dimethoxybenzoic acid imide chloride analogously to Example 1.

The following are obtained analogously:

from "G" and N-isopropyl-3,4-dimethoxybenzoic acid imide chloride
5-[1-(N-isopropyl-3,4-dimethoxybenzimidoyl)-1,2,3,4-tetrahydroquinolin-6-yl]-3,6-dihydro-2H-1,3,4-thiadiazin-2-one;

from "G" and N-cyclopentyl-3,4-dimethoxybenzoic acid imide chloride
5-[1-(N-cyclopentyl-3,4-dimethoxybenzimidoyl)-1,2,3,4-tetrahydroquinolin-6-yl]-3,6-dihydro-2H-1,3,4-thiadiazin-2-one;
from "G" and N-(2-methylbutyl)-3,4-dimethoxybenzoic acid imide chloride
5-[1-(N-(2-methylbutyl)-3,4-dimethoxybenzimidoyl)-1,2,3,4-tetrahydroquinolin-6-yl]-3,6-dihydro-2H-1,3,4-thiadiazin-2-one;
from "G" and N-ethyl-3,4-dimethoxybenzoic acid imide chloride
5-[1-(N-ethyl-3,4-dimethoxybenzimidoyl)-1,2,3,4-tetrahydroquinolin-6-yl]-3,6-dihydro-2H-1,3,4-thiadiazin-2-one;
from "G" and N-cyclopropyl-3,4-dimethoxybenzoic acid imide chloride
5-[1-(N-cyclopropyl-3,4-dimethoxybenzimidoyl)-1,2,3,4-tetrahydroquinolin-6-yl]-3,6-dihydro-2H-1,3,4-thiadiazin-2-one;
from "G" and N-methyl-3-chloro-4-methoxybenzoic acid imide chloride
5-[1-(N-methyl-3-chloro-4-methoxybenzimidoyl)-1,2,3,4-tetrahydroquinolin-6-yl]-3,6-dihydro-2H-1,3,4-thiadiazin-2-one, hydrochloride m.p. 252°;
from "G" and N-isopropyl-3-chloro-4-methoxybenzoic acid imide chloride
5-[1-(N-isopropyl-3-chloro-4-methoxybenzimidoyl)-1,2,3,4-tetrahydroquinolin-6-yl]-3,6-dihydro-2H-1,3,4-thiadiazin-2-one;
from "G" and N-phenyl-3,4-dimethoxybenzoic acid imide chloride
5-[1-(N-phenyl-3,4-dimethoxybenzimidoyl)-1,2,3,4-tetrahydroquinolin-6-yl]-3,6-dihydro-2H-1,3,4-thiadiazin-2-one;
from "G" and N-phenyl-3-chloro-4-methoxybenzoic acid imide chloride
5-[1-(N-phenyl-3-chloro-4-methoxybenzimidoyl)-1,2,3,4-tetrahydroquinolin-6-yl]-3,6-dihydro-2H-1,3,4-thiadiazin-2-one.

The examples below relate to pharmaceutical formulations which contain the compounds of the formula I or their acid addition salts.

EXAMPLE A: TABLETS

A mixture of 1 kg of 5-[1-(N-ethyl-3,4-dimethoxybenzimidoyl)-1,2,3,4-tetrahydroquinolin-6-yl]-6-methyl-3,6-dihydro-2H-1,3,4-thiadiazin-2-one, 10 kg of lactose, 6 kg of microcrystalline cellulose, 6 kg of potato starch, 1 kg of polyvinylpyrrolidone, 0.8 g of talc and 0.1 kg of magnesium stearate is pressed into tablets in the customary manner such that each tablet contains 10 mg of active compound.

EXAMPLE B: COATED TABLETS

Tablets are pressed analogously to Example A and are subsequently coated in the customary manner with a coating of sucrose, potato starch, talc, tragacanth and coloring substance.

EXAMPLE C: CAPSULES

Hard gelatine capsules are filled with 1 kg of 5-[1-(N-butyl-3,4-dimethoxybenzimidoyl)-4,4-dimethyl-1,2,3,4-tetrahydroquinolin-6-yl]-6-methyl-3,6-dihydro-2H-1,3,4-thiadiazin-2-one in the customary manner such that each capsule contains 5 mg of active compound.

EXAMPLE D: AMPOULES

A solution of 1 kg of 5-[1-(N-ethyl-p-fluorobenzimidoyl)-1,2,3,4-tetrahydroquinolin-6-yl]-6-methyl-3,6-dihydro-2H-1,3,4-thiadiazin-2-one in 30 l of 1,2-propanediol is subjected to sterile filtration, and ampoules are filled with the solution, lyophilised under sterile conditions and subjected to sterile sealing. Each ampoule contains 2 mg of active compound.

Tablets, coated tablets, capsules and ampoules which contain one of the other active compounds of the formula I and/or their physiologically acceptable acid addition salts can be obtained analogously.

What is claimed is:
1. A thiadiazinone compound of formula I

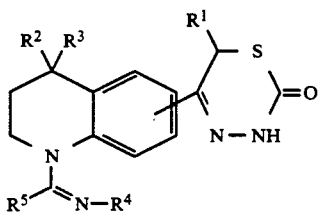

wherein
$R^1$, $R^2$ and $R^3$ are each H or A,
$R^4$ is H, A, Ar, Ar-alkyl or $C_{3-7}$-cycloalkyl,
$R^5$ is A, Ar or $C_{3-7}$-cycloalkyl,
A is $C_{1-8}$-alkyl,
Ar is an unsubstituted phenyl radical or a phenyl radical mono-, di- or trisubstituted by A, OH, OA, $SR^6$, $SOR^6$, $SO_2R^6$, $NO_2$, CO—A, O—$CH_2$—O, Hal, $NH_2$, NHA or $NA_2$,
"-alkyl" is alkylene having 1–5 C atoms,
$R^6$ is A or Ar and
Hal is F, Cl, Br or I
or a physiologically acceptable salt thereof.

2. A compound according to claim 1, wherein
$R^4$ is alkyl having 1–5 C atoms and
$R^5$ is mono- or disubstituted phenyl.

3. A compound according to claim 1, wherein
$R^1$, $R^2$ and $R^3$ are each H or methyl,
$R^4$ is cycloalkyl and
$R^5$ is mono- or disubstituted phenyl.

4. A compound according to claim 1, wherein
$R^1$, $R^2$ and $R^3$ are each H or methyl,
$R^4$ is H and
$R^5$ is mono- or disubstituted phenyl.

5. A compound according to claim 1, wherein
$R^1$, $R^2$ and $R^3$ are each H or methyl,
$R^4$ is alkyl having 1–5 C atoms and
$R^5$ is p-fluorophenyl, 3-chloro-4-methoxyphenyl or 3,4-dimethoxyphenyl.

6. A compound according to claim 1, wherein
$R^1$, $R^2$ and $R^3$ are each H or methyl,
$R^4$ is cycloalkyl and
$R^5$ is p-fluorophenyl, 3-chloro-4-methoxyphenyl or 3,4-dimethoxyphenyl.

7. A compound according to claim 1, wherein
$R^1$, $R^2$ and $R^3$ are each H or methyl,
$R^4$ is H and
$R^5$ is p-fluorophenyl, 3-chloro-4-methoxyphenyl or 3,4-dimethoxyphenyl.

8. a) 5-[1-(N-Isopropyl-3,4-dimethoxybenzimidoyl)-1,2,3,4-tetrahydroquinolin-6-yl]-6-methyl-3,6-dihydro-2H-1,3,4-thiadiazin-2-one;

b) 5-[1-(N-cyclopentyl-3,4-dimethoxybenzimidoyl)-1,2,3,4-tetrahydroquinolin-6-yl]-6-methyl-3,6-dihydro-2H-1,3,4-thiadiazin-2-one;

c) 5-[1-(N-(2-methylbutyl)-3,4-dimethoxybenzimidoyl)-1,2,3,4-tetrahydroquinolin-6-yl]-6-methyl-3,6-dihydro-2H-1,3,4-thiadiazin-2-one;

d) 5-[1-(N-ethyl-3,4-dimethoxybenzimidoyl)-1,2,3,4-tetrahydroquinolin-6-yl]-6-methyl-3,6-dihydro-2H-1,3,4-thiadiazin-2-one;

e) 5-[1-(N-1-butyl-3,4-dimethoxybenzimidoyl)-1,2,3,4-tetrahydroquinolin-6-yl]-6-methyl-3,6-dihydro-2H-1,3,4-thiadiazin-2-one;

f) 5-[1-(N-ethyl-4-fluorobenzimidoyl)-1,2,3,4-tetrahydroquinolin-6-yl]-6-methyl-3,6-dihydro-2H-1,3,4-thiadiazin-2-one; or g) 5-[1-(3,4-dimethoxybenzimidoyl)-1,2,3,4-tetrahydroquinolin-6-yl]-6-methyl-3,4-dihydro-2H-1,3,4-thiadiazin-2-one, each of compound of claim 1.

9. A pharmaceutical composition comparing at least one compound of claim 1 and a pharmaceutically acceptable carrier.

10. A method for the treatment of cardiac insufficiency or hypertension, comprising administering an effective amount of a compound of claim 1.

* * * * *